United States Patent [19]
Earthman

[11] Patent Number: 6,120,466
[45] Date of Patent: *Sep. 19, 2000

[54] SYSTEM AND METHOD FOR QUANTITATIVE MEASUREMENTS OF ENERGY DAMPING CAPACITY

[75] Inventor: James C. Earthman, 6 Virgil Ct., Irvine, Calif. 92612

[73] Assignees: James C. Earthman, Irvine; Cherilyn G. Sheets, Newport Beach, both of Calif.; a part interest

[ * ] Notice: This patent issued on a continued prosecution application filed under 37 CFR 1.53(d), and is subject to the twenty year patent term provisions of 35 U.S.C. 154(a)(2).

[21] Appl. No.: 08/997,490

[22] Filed: Dec. 23, 1997

Related U.S. Application Data
[60] Provisional application No. 60/033,547, Dec. 27, 1996.

[51] Int. Cl.[7] .................................................. A61B 5/103
[52] U.S. Cl. ..................... 600/590; 600/552; 600/553; 600/589; 433/72; 433/215
[58] Field of Search ....................... 600/552, 553, 600/587, 589, 590; 33/513, 514; 433/72, 99, 107, 112, 114, 117, 118, 121, 150, 151, 215; 73/11.01, 12.01, 82

[56] References Cited

U.S. PATENT DOCUMENTS

| | | | |
|---|---|---|---|
| 3,722,100 | 3/1973 | Weisman et al. ..................... 32/40 R |
| 4,341,519 | 7/1982 | Kuhn et al. ............................ 433/122 |
| 4,482,324 | 11/1984 | Wohlgemuth ......................... 433/215 |
| 4,499,906 | 2/1985 | Wohlgemuth et al. ............... 600/589 |
| 4,689,011 | 8/1987 | Wohlgemuth ......................... 433/121 |
| 4,764,114 | 8/1988 | Jeffcoat et al. ....................... 433/72 |
| 5,144,753 | 9/1992 | Murphy ................................ 33/514 |
| 5,318,442 | 6/1994 | Jeffcoat et al. ....................... 433/72 |
| 5,518,008 | 5/1996 | Cucchiaro et al. ................... 600/590 |

*Primary Examiner*—Charles Marmor, II
*Attorney, Agent, or Firm*—Knobbe, Martens, Olson and Bear, LLP

[57] ABSTRACT

A method and system for measuring quantitatively the energy damping capacity of a specimen. In one embodiment of the present invention, the tip of the polymer sleeve of the handpiece of the system is placed directly against the specimen to be tested. The alignment of the handpiece is aided by the polymer tip which maintained the handpiece approximately orthogonal to the specimen surface and a level indicator for aiding the user to keep the handpiece approximately horizontal. Upon the pressing of a finger switch on the handpiece, a magnetic coil within the handpiece propels a tapping rod strikes the specimen multiple times per cycle creating stress waves that traveled through the tapping rod. Vibrations are attenuated by the polymer sleeve so as to not disturb the sensitive measurements. An accelerometer within the handpiece coupled with the tapping rod measures signals corresponding to the resulting stress waves. Data transmitted by the accelerometer is processed by a calibrated computer program which detects changes in the properties of the specimen and quantifies objectively internal characteristics.

28 Claims, 4 Drawing Sheets

SYSTEM AND METHOD FOR QUANTITATIVE MEASUREMENTS OF ENERGY DAMPING CAPACITY

PRIORITY CLAIM

We hereby claim the benefit under 35 U.S.C. § 119(e) of U.S. Provisional Application No. 60/033,547 filed Dec. 27, 1996, entitled "Methods and Apparatus for Preventing and Reversing Tooth Intrusion in Implant-Assisted Prostheses."

BACKGROUND OF THE INVENTION

A method and system that is portable, lightweight and economical for detecting changes in the mechanical properties of components and objectively quantifying internal characteristics would be invaluable to a broad spectrum of professionals.

In the field of dentistry, the stability of a tooth is used as an indicator of the health of the interior of the tooth, the surface of the tooth as well as surrounding structures. A tooth is not part of the alveolar bone, but is connected to the bone by the periodontal ligament. The periodontal ligament, which has a higher damping capacity than enamel, dentin, or bone, dissipates the impact energy of occlusion. Thus, periodontal structural changes lead to changes in tooth mobility. Furthermore, periodontal structural changes are also reflected in the energy damping characteristics of the periodontium.

Periodontal diseases which are very common were traditionally subjectively diagnosed by visual examination of gum inflammation, the periodontal pocket, radiographs of bone atrophy, and tooth mobility. The first attempts to objectively measure tooth mobility used static measurement procedures which investigated the static deflection of the tooth due to a pre-selected horizontal force. An early attempt at dynamic measurement procedures used a non-contact displacement transducer. However, the procedures required a stable mechanical reference system which included attachment to all the teeth except the tooth under examination.

The next advancement in the art was the Siemens Periotest as described by Lukas and Schulte and by the manufacturer, Siemens. This instrument had a handpiece which upon the pressing of a finger switch created a reproducible percussive force using a magnetic coil and a tapping rod. The deceleration of the tapping rod on impact with the tooth was measured by an accelerometer installed in the handpiece.

An analysis of the accelerometer readings indicated a correlation between the contact time and tooth mobility. This contact time was used to calculate a Periotest value which determined the appropriate category of tooth mobility. Under such a system, a Periotest value greater than or equal to thirty translated into a category III mobility which meant that the tooth could be moved with labial pressure. A Periotest value greater than or equal to twenty, but less than thirty, translated into a category II mobility which meant that mobility could be seen. A Periotest value greater than or equal to ten, but less than twenty, translated into a category I mobility which meant that mobility could be felt. A Periotest value greater than or equal to negative eight, but less than ten, translated into a category zero mobility which meant that the tooth was securely anchored.

The Siemens Periotest had several limitations. The first obstacle to accurate and reproducible readings was that the pen-shaped handpiece had to be held with the tip of its metal sleeve located between 0.5 millimeters to 2.5 millimeters from the tooth. The tip of the metal sleeve could not touch the tooth during the measurement procedure because, among other reasons, stress waves would propagate through the metal sleeve up the casing of the handpiece distorting readings. Maintaining the tip of the metal sleeve of the handpiece within the minuscule range proved a cumbersome requirement for a hand-held device. Error in judging such minuscule distances and the subsequent placement of the handpiece outside the small range of distances could be the sole cause of aberrant readings. Furthermore, variations in tip to tooth distances from measurement procedure to measurement procedure caused variations in data. Deviations placing the tip of the metal sleeve outside of the range of 0.5 millimeters to 2.5 millimeters occurred from the natural shaking of the hand which held the device or from the shaking of the device derived from the pressing of the finger switch located on the handpiece, or from the shaking of the handpiece during the measurement procedure.

The second obstacle to consistent and accurate readings was that the handpiece had to be maintained in a horizontal position. Even a small angle from the horizontal would create significant errors in the measurement due to gravity and friction affecting the kinetic energy of the tapping rod. Keeping the handpiece in a substantially horizontal position was especially difficult where the operator was holding the handpiece in the air with a focus on keeping the tip of the metal sleeve of the handpiece between 0.5 millimeters to 2.5 millimeters from the tooth and where the operator was physically pushing a finger switch on the handpiece to activate the measurement procedure. Both the distance between the tip of the sleeve and the tooth and the angle of inclination of the handpiece had to be consistently maintained during the measurement procedure and in subsequent measurement procedures in order to obtain consistent and accurate results. Moreover, the Siemens Periotest gave no warning or feedback to the operator that the handpiece was at an exorbitant angle before the commencement of the measurement procedure. Neither was the operator given any information regarding the angle at which the measurements were taken.

SUMMARY OF THE INVENTION

The present invention is a system and method for obtaining accurate data concerning the energy damping characteristics of the periodontium. The data provided is reproducible from measurement procedure to measurement procedure in order to determine objectively tooth mobility. This invention maintains a reproducible distance between the tooth and the tip of the sleeve of the handpiece during the measurement procedure and in subsequent measurement procedures upon the same tooth. Furthermore, the invention assists the operator to hold the handpiece at a consistent angle during the measurement procedure and in subsequent measurement procedures upon the same tooth.

In one embodiment of the present invention, the sleeve of the handpiece is of such material and of such length so as to attenuate vibrations that might travel through the sleeve to the casing of the handpiece, and thus interferes with the sensitive measurements. The tip of the sleeve, thus can be placed directly against the specimen. In one embodiment, the flattened tip of the sleeve helps to keep the tip approximately orthogonal to the specimen surface and a level indicator maintained the handpiece in an approximately horizontal position before, during, and in subsequent measurements. The consistent and reproducible positioning of the tip with respect to the specimen creates consistent and reproducible conditions which produced precise and accurate results.

While the present invention provides significant advantages within the field of dentistry, its ability to perform energy damping capacity measurements has many applications beyond dentistry.

DETAILED DESCRIPTION OF THE PREFERRED EMBODIMENT

The system comprises hardware and virtual instrumentation software that perform energy damping capacity measurements on a specimen. The present invention makes it possible to perform an objective, quantitative measurement of energy damping capacity referred to as the loss coefficient, η. The resulting measurements are compared with known and tabulated values in the open literature and found to be not only accurate, but also reproducible and precise. Thus, the present invention provides objective, quantitative information that is very useful, for example, in the evaluation and design of dental implant structures and engineering structures, and in the study of materials and composites.

Figure 1:
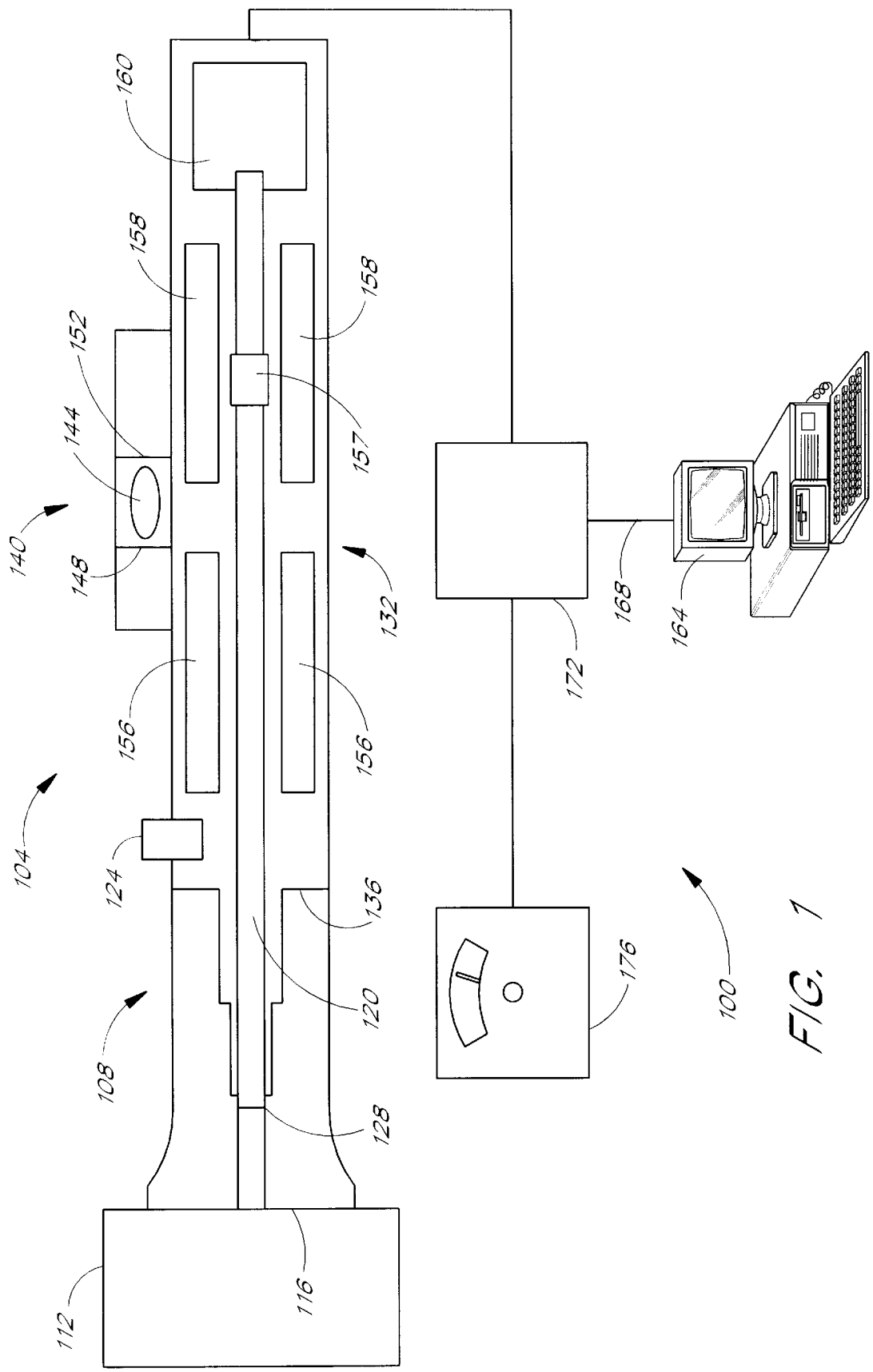
FIG. 1 shows one embodiment for a system and method for quantitative measurements of energy damping capacity.
Figure 2A:
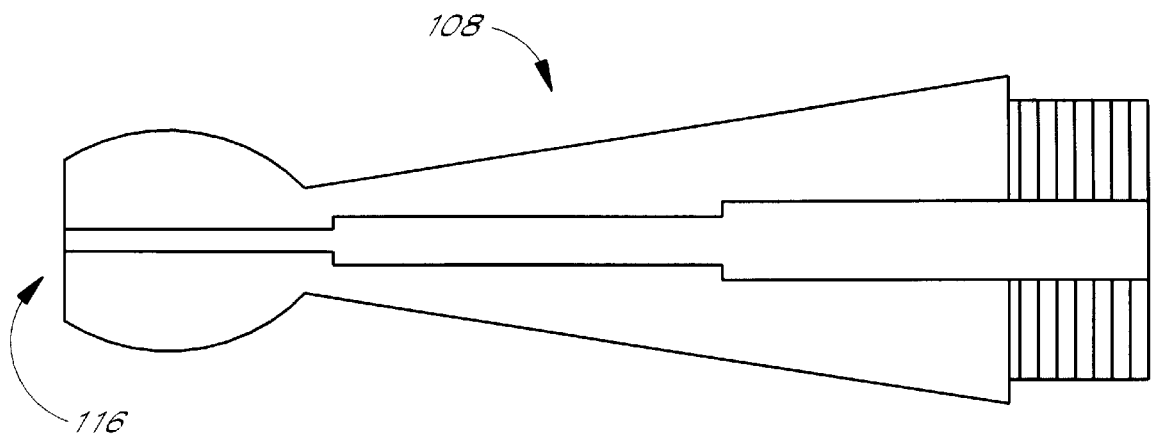
FIG. 2A is an embodiment of the sleeve of the handpiece.
Figure 2B:
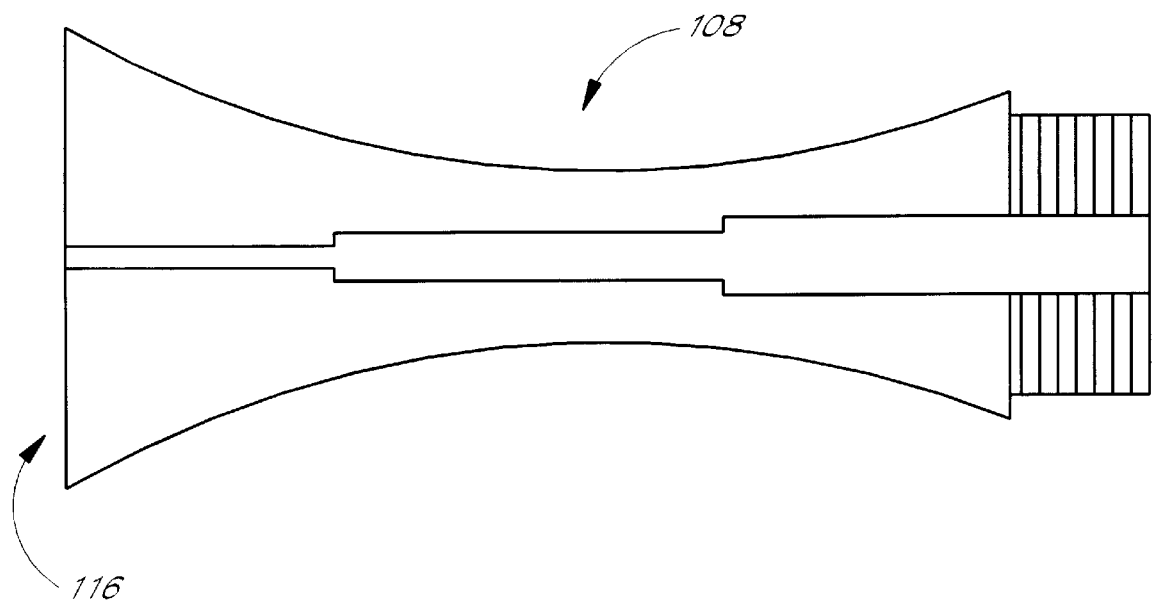
FIG. 2B is an embodiment of the sleeve of the handpiece.
Figure 2C:
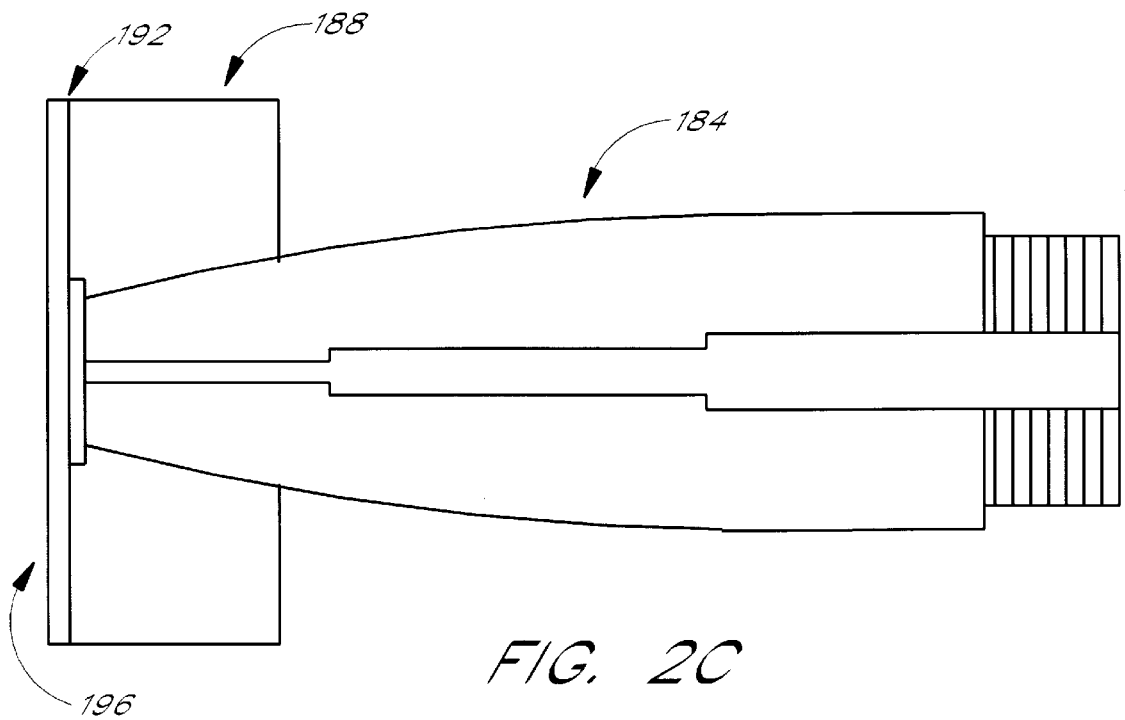
FIG. 2C is an embodiment showing the sleeve of the handpiece with a polymer mass shaped in the form of a disc and high damping tape.
Figure 2D:
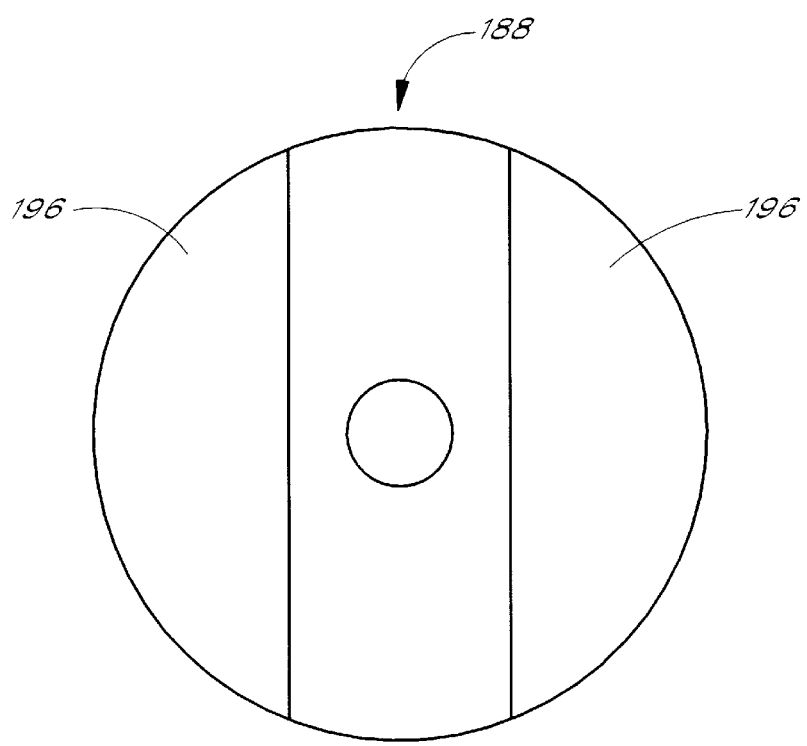
FIG. 2D is a front view showing the sleeve of the handpiece with a polymer mass shaped in the form of a disc and high damping tape.

As shown in FIG. 1, one embodiment of the present system 100 utilizes a handpiece 104 made by Siemens called the Periotest. In this embodiment, a custom polytetrafluoroethylene (PTFE) sleeve 108 is used instead of the prior art metal sleeve located at the tip of the handpiece 104. To commence the testing of a specimen 112, the tip 116 of the sleeve 108 of the handpiece 104 is placed against the specimen 112 and the tapping rod 120 inside the handpiece 104 is activated with the push of a finger switch 124 located on the handpiece 104.

In one specific embodiment of the invention, the polymer sleeve 108 of the handpiece 104 extends out so that the distance from the tip 116 of the polymer sleeve 108 in contact with the specimen 112 to the head 128 of the tapping rod 120 in its retracted stationary position ranges generally from about 3.5 millimeters to about 5.5 millimeters, and preferably from about 3.75 millimeters to about 4.5 millimeters. In one preferred embodiment, the distance from the tip 116 of the polymer sleeve 108 of the handpiece 104 in contact with the specimen 112 to the head 128 of the tapping rod 120 in its retracted stationary position is about 4 millimeters. The polymer sleeve 108 length in one embodiment is dependent upon the length of the tapping rod 120 and the total distance that the tapping rod 120 can travel when activated without a significant degradation in forward progress due to friction and gravity. In another embodiment, the handpiece casing 132 is made of the same material as the polymer sleeve 108. The other end 136 of the polymer sleeve 108 is threaded so that it connects to the handpiece casing 132 with a similar threading. The plane comprising the specimen end 116 of the polymer sleeve 108 is approximately orthogonal to the axis of the handpiece. Further, the surface area of the specimen end 116 of the polymer sleeve 108 is sufficiently large to assist in the approximately orthogonal placement and position stability of the handpiece 104. In one embodiment, the outer diameter of the specimen end of the tip 116 is generally within the range of from about 6 millimeters to about 14 millimeters, and preferably within the range of from about 8 millimeters to about 11 millimeters. In one preferred embodiment, the outer diameter is about 9.5 millimeters. The inner diameter of the specimen end of the tip is generally within the range of from about 3 millimeters to about 6 millimeters, and preferably within the range of from about 4 millimeters to about 5 millimeters. In one preferred embodiment, the inner diameter is about 4.7 millimeters.

The polymer sleeve also has varying inner diameters which decreases from where the sleeve was threaded 136 to the specimen end 116 of the sleeve 108. FIG. 1 shows one embodiment where the polymer sleeve 108 has three discrete inner diameters. Other embodiments have more or less than three inner diameters, with one embodiment having a continuously, decreasing inner diameter from where the polymer sleeve was threaded 136 to the specimen end 116 of the polymer sleeve 108. Decreasing inner diameters helped guide the tapping rod 120 to strike the specimen 112 in a consistent location and at a consistent angle of inclination.

A significant feature of the invention is the greater accuracy and precision obtained with the polymer sleeve 108 of such damping capacity and of such length so as to attenuate any stress waves that might interfere with the measurement procedure. The tip 116 of the polymer sleeve 108 is placed directly against the specimen 112. By placing the tip 116 of the polymer sleeve 108 of the handpiece 104 directly against the specimen 112, this embodiment of the invention has the advantage of keeping the distance between the specimen 112 and the tip 116 of the polymer sleeve 108 of the handpiece 104 consistently the same, resulting in better data reproducibility and greater accuracy.

This is a significant improvement over the prior art which required that the tip of the prior art metal sleeve of the handpiece be maintained between 0.5 millimeters to 2.5 millimeters from the specimen. The tip of the prior art metal sleeve of the handpiece could not be positioned in direct contact with the specimen because when the measurement procedure commenced and the tapping rod impacted the specimen, a stress wave would propagate from the specimen through the metal sleeve to the rest of the handpiece interfering with the sensitive measurements being taken.

The capability of placing the tip 116 of the polymer sleeve 108 directly against the specimen 112 further enhances measurements over the prior art. In the prior art, an operator had to judge accurately and consistently a distance between 0.5 millimeters to 2.5 millimeters. This was extremely difficult especially when the specimen, perhaps a tooth, might be moving due to, for example, the patient's head shaking ever so slightly during the measurements. Furthermore, in the prior art, not only did an operator have to judge the distance accurately, but the operator had to judge the distance precisely; that is, the operator to be consistent had to set up the handpiece at the same distance over subsequent measurements for the measurements to be truly meaningful.

These concerns are addressed in this embodiment of the present invention where the tip 116 of the polymer sleeve 108 of the handpiece 104 is positioned directly on the specimen 112. As such, the tip 116 of the polymer sleeve 108 is placed consistently against the specimen 112 recreating consistent and accurate measurements essentially independent of the evaluations of the operator and the slight movements in the specimen 112.

Further, because as described, the tip 116 of the polymer sleeve 108 is positioned directly on the specimen 112, it is easier for the operator to hold the handpiece 104 steady and to maintain a consistent distance between the tip 116 of the polymer sleeve 108 and the specimen 112 while measurements were being taken. The polymer sleeve 108 which has a flattened tip 116 assists in aligning of the handpiece 104 approximately orthogonal to the surface of the specimen 112 when the tip 116 is placed in contact with the specimen 112. Self-alignment through contact between the tip 116 and the specimen 112 results in more accurate and precise measurements with the angle at which the tapping rod 120 strikes the specimen 112 being kept constant both during the measurements and in subsequent measurements.

As mentioned above, the use of a polymer for the sleeve 108 of the handpiece 104 results in a cleaner signal by keeping stress waves from propagating up the case 132 of the handpiece 104. In one preferred embodiment, PTFE is used as the sleeve 108 polymer. PTFE is autoclavable and is of sufficiently high damping capacity to attenuate stress waves from the specimen 112. The sleeve 108 material generally has a damping capacity as represented by its loss coefficient, $\eta$, ranging from about 0.03 to about 0.2, and preferably within the range of from about 0.06 to about 0.1. In one preferred embodiment, the loss coefficient was about 0.08. PTFE also has the advantage of being a solid lubricant which reduces friction between the sleeve 108 and the tapping rod 120 as the tapping rod 120 travels back and forth during the measurement procedure.

A level indicator 140 attached to the casing 132 of the handpiece 104 assists the operator in holding the handpiece 104 approximately horizontal during testing. In one embodiment of the present invention, the level indicator 140 comprises an air bubble 144 trapped in a liquid held in a transparent casing. The user simply keeps the air bubble 144 centered between two marks 148 and 152 in the middle of the transparent casing to assure that the handpiece 104 is in an approximately horizontal position. Furthermore, with the assistance of the flattened tip 116 of the polymer sleeve 108 which self-aligned itself with the specimen 112, the operator is further aided in keeping the handpiece 104 approximately horizontal to the ground and approximately orthogonal to the surface of the specimen 112. This solves the problem in the prior art of having the handpiece at an excessive angle to the horizontal during some measurements which would cause inconsistent results and errors due to the effect of gravity and friction on the kinetic energy of the tapping rod in the handpiece.

Upon activation of the finger switch 124 on the handpiece 104, a movable tapping rod 120 is driven by a propulsion coil 156 through an orifice in the sleeve 108 to impact the specimen 112 sixteen times in four seconds. As the tapping rod 120 moves, a magnet 157 located on the tapping rod 120 is displaced with respect to a measuring coil 158. The acceleration of the tapping rod 120 is measured by the accelerometer 160. An accelerometer 160 produced signals corresponding to the shock wave resulting from each impact. These signals were then sent to a high speed data acquisition board housed in a computer 164. In one embodiment, a sixteen bit analog-to-digital channel on a data acquisition card housed in a computer 164 was used. Although a sampling rate of at least about 600 kHz is found to be sufficient for most specimens, a sampling rate of at least about 800 kHz was more preferable.

In one embodiment, a coaxial cable 168 was used to connect the accelerometer signals to the high speed data acquisition card. In another embodiment where the Siemens Periotest base 172 was used, the inner conductor of the cable 168 was connected to pin 8 of an M8806 National Semiconductor integrated circuit within the Siemens Periotest base 172. This pin accessed the signal from the accelerometer 160 in the handpiece 104. The ground/shield conductor of this cable 168 was connected to the signal ground for the Siemens Periotest base 172.

In those embodiments that utilized the Siemens Periotest base 172, it was found that the battery system that came with the Siemens Periotest base 172 was problematic with respect to obtaining reproducible and accurate results. The battery system tended to drift in voltage with time, especially when many measurements were taken before the battery could be recharged. To avoid the problem, a regulated power supply 176 set to 12.7 volts was used to power the Siemens Periotest base 172 instead of the battery system.

In FIG. 2, several other embodiments of the sleeve 108 of the handpiece 104 are shown. In FIGS. 2A and 2B, the polymer sleeves 108 feature flattened tips 116 approximately orthogonal to the specimen 112 surface to further assist with the alignment of the handpiece 104. In FIG. 2B, the outer diameter is at least several times larger than the inner diameter of the sleeve 108. FIG. 2C shows still another embodiment which utilized the metal sleeve 184 of the Siemens Periotest handpiece. A polymer mass 188 in the shape of a disc was form fitted to the end of the metal sleeve 184. The metal sleeve 184 tip is permanently positioned a few millimeters from the specimen end 192 of the polymer mass 188 and thus the metal sleeve 184 is maintained at a constant displacement away from the specimen 112. A high damping capacity tape 196 is also placed on the specimen side 192 of the polymer mass 188. FIG. 2D shows a frontal view of the polymer mass 188 in the shape of a disc, further showing the configuration of the high damping capacity tape 196. Note that the sleeve in FIGS. 2C and 2D does not need to be metal, but can also be polymer. Further, the shape of the form fitted polymer mass 188 need not be in the shape of a disc, but can be cut in a number of other shapes and forms, so long as the shape or form used assists with the approximately orthogonal alignment of the handpiece 104 and attenuated vibrations from the specimen 112 caused by the measurement procedure that might travel through the sleeve 184 and into the casing 132 of the handpiece 104 where sensitive measurements were being taken.

Software stored in the computer 164 acquires and analyzes ten of the sixteen impacts to quantitatively determine the damping capacity of the specimen. Typically, six to ten impacts were preferred for adequate sampling of the loss coefficient for a given specimen.

Figure 3:
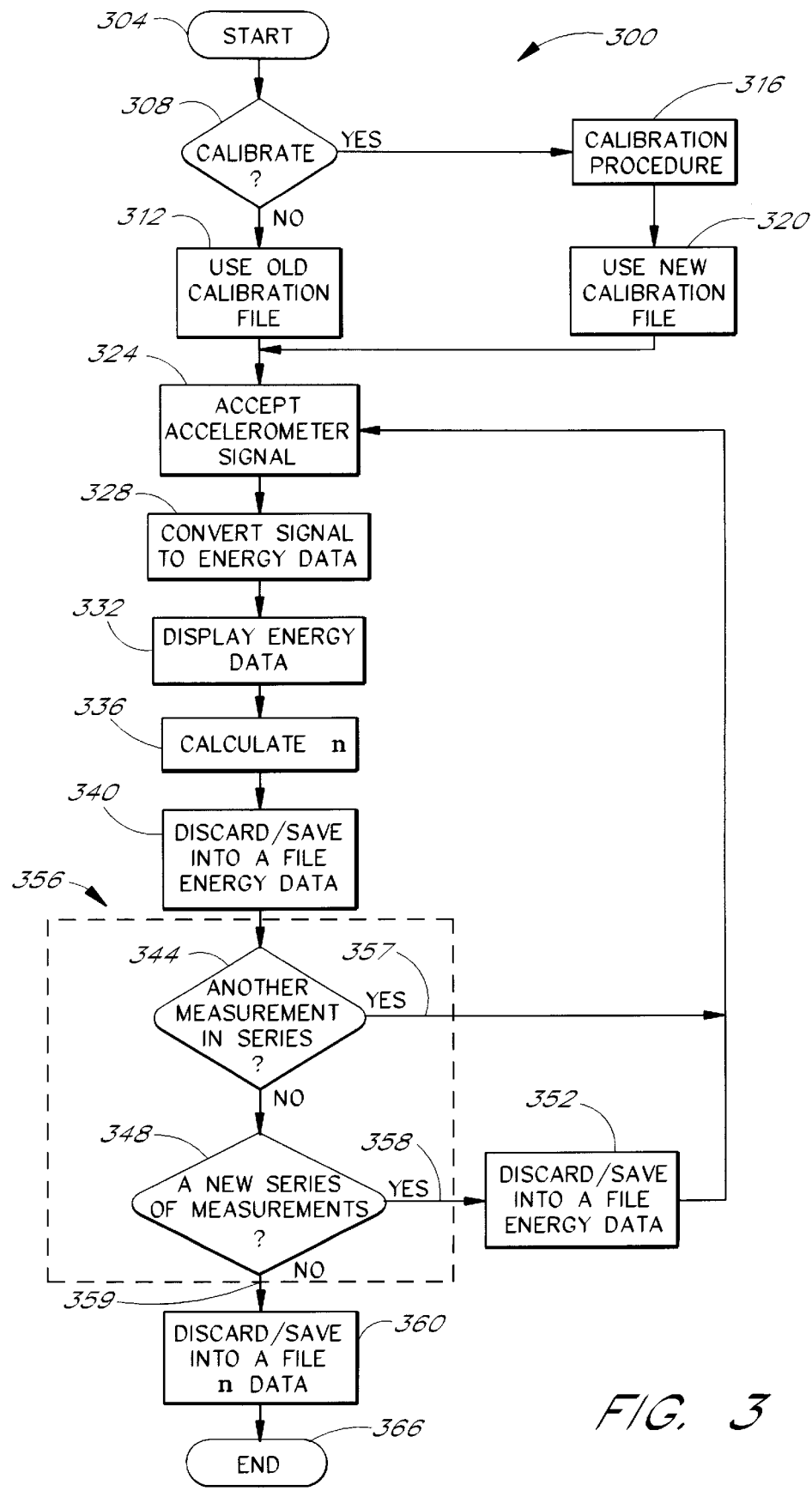
FIG. 3 is a flowchart of the software program.

FIG. 3 shows a flowchart 300 of one embodiment of software procedure. After the program is loaded and executed 304, the next step 308 determines whether calibration is needed. If a familiar testing configuration is to be implemented, then the program loads previously determined calibration values stored in a file 312. A calibration file can be chosen from among the many previous calibration files stored in memory. If a new testing configuration is being used, then a calibration procedure 316 was completed and the new calibration values stored in a new file before the new calibration values are implemented at step 320. In the next step 324, the program accepts the signal from the accelerometer, converted the signal into energy data 328, displaying the energy data in graphical and textual form on the computer monitor 332, calculating the loss coefficient, $\eta$ 336, and then either discarding or saving into a file the energy data depending upon the discretion of the operator 340.

Then, the operator chooses from among three options: make more measurements in that series of measurements 357; commence a new series of measurements 358, or exit the program 359. In one embodiment of the program, a graphical user interface displays the above three options from which the operator could choose. This interface is reflected by the box 356 outlined in the flowchart 300 which has three paths leading out of the box 357, 358 and 359.

If more measurements in the series of measurements are requested 357, the program loops back to the step where the program accepted the signal from the accelerometer 324. If more measurements in the series of measurements are not requested, but instead a new series of measurements are requested, then program either discards or saves into a file the energy data depending upon the discretion of the operator 352 before looping back to the step where the program accepted the signal from the accelerometer 324. If more measurements in the series of measurements are not requested and no new series of measurements are requested 359, then the program is either discarded or saved into a file the loss coefficient data depending upon the discretion of the operator 360 before ending the program 366.

Determination of the Loss Coefficient

The total strain energy, U, for the present system is assumed to be approximately equal to the kinetic energy of the tapping rod 120 just prior to contact with the specimen 112. Thus, the energy dissipated, D, is defined as $$D = U - E_\epsilon - D_p$$

where $E_\epsilon$ is the elastic strain energy conserved and $D_p$ is the energy dissipated by sources external to the specimen 112. Upon impact, the elastic strain energy, $E_\epsilon$, is returned to the tapping rod 120 in the form of a stress wave.

Damping refers to the ability of a solid to dissipate mechanical energy. Damping capacity was characterized by the loss coefficient or loss factor, $\eta$, which was given by $$\eta = \left(\frac{1}{2\pi}\right)\frac{D}{U}$$

where the factor of $2\pi$ existed in the denominator to normalize the value of $\eta$ per radian, as most materials were tested for damping capacity under cyclic loading.

Substituting for D, the loss coefficient thus is given as $$\eta = \frac{1}{2\pi}\left[1 - \frac{E_\epsilon + D_p}{U}\right].$$

The kinetic energy of the tapping rod 120 prior to impact is determined by measuring the mass and velocity of the tapping rod 120 just prior to contact with the specimen 112. For example, in one embodiment, the average value was determined to be about $3.3 \times 10^{-6}$ joules.

Calibration

In order to calibrate a given embodiment of the invention, the acceleration of the tapping rod 120 before and during impact is measured for model materials with known characteristics. The statistical variation of the material measurements is determined, thus providing an assessment of the overall accuracy and precision of the method and instrumentation. The standard deviation of the data for each material is determined for the maximum strain energy returned from the specimen 112 and its loss coefficient.

The elastic strain energy conserved is given by $$E_\epsilon = C\ F^2$$

where the constant, C, varies inversely with the effective elastic modulus of the tapping rod 120 and the force, F, is proportional to both the mass of the tapping rod 120 and the maximum acceleration of the tapping rod 120 as a result of the stress wave created from the impact. The value of $D_p$ which represents the energy dissipated by sources external to the specimen 112 did not vary significantly with different material specimens since it primarily depends on the energy losses in the handpiece 104, not the specimen 112. Thus, it is reasonable to assume that $D_p$ is relatively constant for a given testing configuration and for a given tapping rod 120. To determine the values of C and $D_p$, it was useful to measure the elastic strain energy conserved for two model materials that have known loss coefficient values, $\eta_1$ and $\eta_2$. By substituting equations and rearranging terms, the value of C was then given by $$C = C_{1,2} = \frac{2\pi U(\eta_1 - \eta_2)}{F_1^2 - F_2^2}$$

where the subscripts 1 and 2 referred to the first and second model materials respectively. A determination of the value of C for the given testing configuration and tapping rod 120 then resulted in a determination of the value of $D_p$ given by $$D_p = D_{p1,2} = U\ (1 - 2\pi\eta_{1,2}) - C\ F_{1,2}^2$$

for either of the two model materials, thus completing calibration.

Other Applications

The present invention has application in the detection of internal damage comprised of microcracking and delamination in composite structures and other engineering materials. Composites are generally more susceptible to damage development than were unreinforced metals, particularly when they were under stresses that approach the tensile strength of the material. The present invention is useful for detecting damage through nondestructive testing in composite materials and structures.

Prior art damping test machines were generally large and bulky and required test specimens cut to specific dimensions. The present invention is able to test specimens of practically any size and shape. Although originally designed for measuring the damping characteristics of teeth and dental implant structures, the invention is applicable to a variety of other applications where the measurement of damping characteristics is utilized. Other applications include, but are not limited to, testing airplane structures, composite structures, engineering materials, or the secureness of medical implants. The present instrumentation is particularly advantageous in locations that were difficult to access or where liquid couplants could not be used. Furthermore, the present invention can be used to test for structural integrity, the looseness of a screw, cracks in teeth as well as bone, and damage in integrated circuit materials. However, the above list is not intended to be exhaustive.

What is claimed is:

1. A system for providing energy damping capacity measurements, comprising:
   a handpiece having
      a front end;
      a sleeve adapted to be placed directly against a specimen, said sleeve being located at the front end of said handpiece for attenuating vibrations created during said measurements;
      a movable tapping rod within said handpiece having one end extending through said handpiece; and
      an accelerometer within said handpiece; and
   a programmed digital computer coupled to said accelerometer, said computer processing the data transmitted by said accelerometer for measuring quantitatively the energy damping capacity of said specimen.

2. A system for providing energy damping capacity measurements, comprising:
   a handpiece having a length, a front end, and a back end, said handpiece comprising a sleeve located at said front end,
   said sleeve attenuating vibrations created during said measurements, and
   said sleeve adapted to be placed directly against a specimen.

3. The system in claim 2 wherein said sleeve has a loss coefficient ranging from about 0.03 to about 0.2.

4. The system in claim 2 wherein said sleeve has a loss coefficient ranging from about 0.06 to about 0.1.

5. The system in claim 2 wherein said sleeve has a loss coefficient of about 0.08.

6. The system in claim 2 wherein said sleeve comprises polytetrafluroethylene.

7. The system in claim 2 wherein said sleeve comprises a flattened tip.

8. The system in claim 2 wherein said sleeve is autoclavable.

9. The system in claim 2 wherein said sleeve is a solid lubricant.

10. The system in claim 2 wherein said sleeve comprises an orifice through which a tapping rod travels, said orifice with a decreasing diameter.

11. The system in claim 2 wherein said sleeve comprises a polymer mass, said polymer mass having a flattened tip and form fitted around the end of said sleeve.

12. The system in claim 11 wherein said sleeve further comprises a high energy damping capacity tape attached to said flattened tip of said polymer mass.

13. The system in claim 2 wherein said handpiece has a loss coefficient ranging from about 0.03 to about 0.2.

14. The system in claim 2 further comprises a level indicator on said handpiece.

15. The system in claim 2 further comprises a regulated power supply coupled to said handpiece.

16. The system in claim 2 further comprises a computer coupled to said handpiece.

17. The system in claim 16 wherein said computer comprises a data acquisition card, a data acquisition card controller coupled to said data acquisition card, and output data from said data acquisition card.

18. The system in claim 17 wherein said data acquisition card is set to a sampling rate of at least about 600 kHz.

19. The system in claim 17 wherein said data acquisition card is set to a sampling rate of at least about 800 kHz.

20. The system in claim 17 wherein said computer comprises a data analyzer to manipulate said output data.

21. The system in claim 20 further comprises a monitor to display in graphical and textual form said manipulated output data from said data analyzer.

22. The system in claim 17 wherein said computer comprises a data analyzer to manipulate said output data into energy data and loss coefficients.

23. A method for providing energy damping capacity measurements of a specimen, comprising the steps of:
   placing a sleeve of a handpiece directly against said specimen,
   keeping said handpiece approximately orthogonal to the plane containing the surface of said specimen,
   maintaining said handpiece approximately horizontal, and
   converting measurement signals from said handpiece into energy data and loss coefficients.

24. The method in claim 23 including the step of positioning a flattened tip of the sleeve approximately flat against the surface of said specimen.

25. The method in claim 23 including the step of using a level indicator as a continuous feedback device to maintain said handpiece approximately horizontal.

26. The method in claim 23 further comprising the step of displaying said energy data and loss coefficients through a graphical user interface.

27. The method in claim 23 further comprising the step of maintaining a regulated level of voltage applied to said handpiece.

28. A method for testing the stability of a tooth and the health of the periodontium, comprising the steps of:
   placing a sleeve of a handpiece directly against said tooth,
   providing a means for attenuating vibrations attempting to propagate through said sleeve to the rest of said handpiece,
   keeping said handpiece approximately orthogonal to the plane containing the surface of said tooth,
   maintaining said handpiece approximately horizontal, and
   converting measurement signals from said handpiece into energy data and loss coefficients.

* * * * *